United States Patent [19]

Corda et al.

[11] Patent Number: 4,459,308

[45] Date of Patent: Jul. 10, 1984

[54] PYRETHROIDS

[75] Inventors: Francesco Corda; Franco Gozzo, both of Milan; Vincenzo Caprioli, Pavia, all of Italy

[73] Assignee: Montedison S.p.A., Milan, Italy

[21] Appl. No.: 287,030

[22] Filed: Jul. 27, 1981

[30] Foreign Application Priority Data

Jul. 29, 1980 [IT] Italy .................. 23769 A/80

[51] Int. Cl.$^3$ ............... A01N 53/00; C07D 307/16; C07C 121/75
[52] U.S. Cl. ................ 424/285; 260/465 D; 424/304; 424/305; 549/496; 549/499; 560/124
[58] Field of Search ............ 260/465 D; 560/124; 549/496, 499; 424/304, 305, 285

[56] References Cited

U.S. PATENT DOCUMENTS

| | | | |
|---|---|---|---|
| 4,183,948 | 1/1980 | Huff | 424/304 |
| 4,224,227 | 9/1980 | Martel et al. | 260/347.4 |
| 4,328,237 | 5/1982 | Piccardi et al. | 424/274 |

Primary Examiner—Dolph H. Torrence
Attorney, Agent, or Firm—Morgan, Finnegan, Pine, Foley & Lee

[57] ABSTRACT

There are described 2,2-dimethyl-cyclopropanecarboxylates having in position 3 of the cyclopropane ring, a polyhalogenated chain having from 3 to 6 carbon atoms.

Said compounds are insecticide and acaricide compounds with a high activity and long persistence.

There is also described the use of the above mentioned compounds, as well as the synthesys processes and the corresponding intermediates.

6 Claims, No Drawings

PYRETHROIDS

The present invention concerns new insecticides belonging to the class of synthetic pyrethroides, and more particularly it relates to 2,2-dimethyl-cyclopropanecarboxylic esters carrying in position 3 of the cyclopropane ring a polyhalogenated chain having from 3 to 6 carbon atoms; moreover, the invention also concerns the use of said compounds against infestations by noxious insects, the process for the preparation of said compounds as well as the corresponding intermediates.

Synthetic pyrethroids are compounds which derive from modifications of the pyrethrum molecule, an insecticide of a natural origin that is endowed with good characteristics such as a high insecticide activity and a low toxicity for mammals (hot-blooded animals).

Natural pyrethrum shows, however, a few drawbacks, amongst which a rather high photo-oxidability, wherefore the molecule decays in a very short time and, thus, the insecticide activity turns out to be too little persistent.

In order to overcome such drawbacks whilst, at the same time maintaining the desirable high insecticide activity and the low toxicity, there have been carried out some modifications on the molecule which have led to the creation of synthetic pyrethroids.

There are known quite a number of synthetic pyrethroids, some of which have been collected by M. Elliott in "Synthetic Pyrethroids—ACS—Symposium Series n. 42 Washington (1977)".

We have now found, and this forms the object of this invention, compounds having the general formula:

(I)

wherein:
X and X' (equal to or different from each other)=Cl or Br;
Y=H, F, Cl, Br;
Y'=CF$_3$, $-CH=C\diagup^{Z}_{Z'}$ ;

Z=F, Cl, Br, CH$_3$, CF$_3$;
Z'=F, Cl, Br, CF$_3$;
R=halogen (Cl, Br), OH, OR$^1$, OR$^2$;
R$^1$=alkyl with from 1 to 4 carbon atoms $R^2 = -\overset{R^3}{\underset{|}{CH}}-\bigcirc\!\!-O-\bigcirc$ or -continued and
R$^3$=H, CN, —C≡CH.

The compounds of formula I, wherein R=OR$^2$, are pyrethroids endowed with a high insecticide and acaricide activity and have a good persistence, while the compounds of formula I, wherein R=halogen, OH, OR$^1$, are intermediates for the synthesis of the pyrethroids of formula I.

The synthesis of the compounds of formula I may be achieved according to various different processes which involve reactions generally known in the normal procedures of organic chemistry.

A first useful process for preparing the compounds of formula I, in which X=X', consists in adding halogen (Cl$_2$ or Br$_2$) to the compounds of the formula:

(II)

(wherein Y, Y' and R have the same meanings as those reported for formula I).

The compounds of formula II, wherein R=OR$^2$, are likewise pyrethroids and have been described, together with the corresponding intermediates of formula II, wherein R=halogen, OH or OR$^1$, in the following patent applications: British Pat. appl. No. 2.015.519 (Montedison S.p.A.), Italian Patent application No. 27542A/79 (Montedison S.p.A.), British Patent application No. 2.000.764 (Imperial Chemical Industries).

The halogenation of the compounds of formula II may conveniently be carried out using known methods of addition of halogen to a double bond, and may be carried out both on compounds of formula II in which R is a halogen, an OH, OR$^1$ group, as well as on compounds of formula II in which R=OR$^2$.

The reactions which, starting from the compounds of formula II, lead to the compounds of formula I, are reported on the following scheme 1 and thereafter commented.

Scheme 1:

(II, R = OR$^1$) $\xrightarrow{\text{Cl}_2 \text{ or Br}_2}$ (I, R = OR$^1$)

↓2  ↓2a

Scheme 1:

-continued

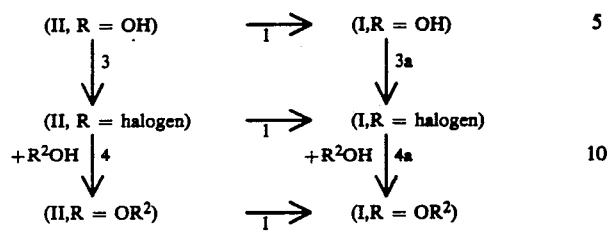

[X = X' = Cl or Br; Y, Y', $R^1$ and $R^2$ have the meanings reported for general formula I].

The halogenation of the compounds of formula II, reported in scheme 1 (reaction 1), may be carried out in different known ways, the choice of which depends mainly on the substrate (compound of formula II) that has to be halogenated.

Among these various known methods there may be mentioned the direct halogenation which is achieved by adding to a solution of the compound of formula II in an inert solvent, maintained under stirring at between 0° and 50° C., a substantially equimolar amount of a halogen ($Cl_2$ or $Br_2$), optionally dissolved (in the case in which the halogen be $Br_2$) in the same inert solvent.

Suitable solvents may be chlorinated or aromatic hydrocarbons.

Other suitable methods consist in using as halogenating agent a complexed halogen, for instance complexed with pyridine or pyridine bromohydrate.

In this case the reaction will be conducted in polar solvents such as acetic acid or pyridine, and may optionally be carried out in the absence of light.

The reaction sequence 2-3-4, which leads to the obtention of the pyrethroids of formula II ($R=OR^2$), consists in the hydrolysis of the alkyl esters of formula II wherein $R=OR^1$, in the conversion of the thus obtained carboxylic acid ($R=OH$) to the corresponding acyl halide ($R=$halogen) and in the subsequent reaction of this latter with an alcohol of the formula: $R^2$—OH.

Said reaction sequence has been described in the previously cited patent applications.

Reaction 2a (hydrolysis of the compounds of formula I in which $R=OR^1$), reaction 3a (conversion of the carboxylic acids of formula I in which $R=OH$ into the corresponding acyl halides wherein $R=$halogen) and 4a (reaction of the acyl halides with alcohols of the formula $R^2OH$) are altogether analogous to the corresponding reactions 2, 3 and 4.

A second process for the synthesis of the compounds of formula I comprises the not contemporaneous introduction of the two halogen atoms X and X', before the formation of the cyclopropane ring.

Said process, which is carried out according to normal reactions of organic chemistry, is useful for the preparation of both the compounds of formula I, in which X is equal to X', as well as for the preparation of compounds in which X is different from X'.

The reactions that constitute this second process are reported in following scheme 2 and are then suitably commented.

Scheme 2:

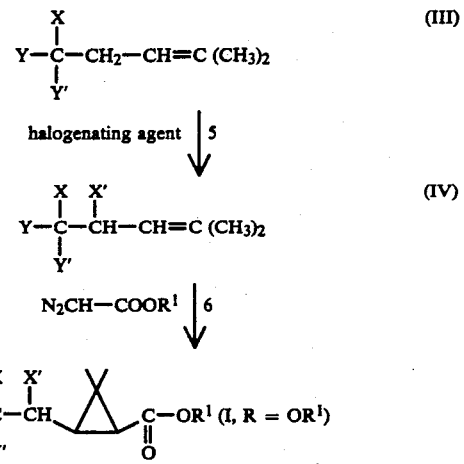

[X, X', Y, Y' and $R^1$ have the meanings indicated for general formula I].

Reaction 5 consists in a halogenation in an allylic position of the compounds of formula III, by using suitable halogenating agents.

Depending on the halogen (X') that one wishes to introduce, there may be cited as suitable halogenating agents: chlorine ($Cl_2$), bromine ($Br_2$), N-chloro or N-bromosuccynimide or $SO_2Cl_2$.

The compounds of formula III are known compounds or easily preparable according to well known techniques.

Reaction 6 consists in treating intermediate IV, as obtained from reaction 5, with a diazoacetate of the formula $N_2CH$—$COOR^1$. The reaction may be conducted in an inert solvent and in the presence of metal copper and copper salts as catalysts.

Thereby there are obtained the compounds of formula I wherein $R=OR^1$ (lower alkyl esters), from which it is possible to then prepare the other compounds of formula I, operating according to reactions 2a, 3a, and 4a as reported in scheme 1.

The compounds of formula I may present themselves as mixtures of geometrical and configurational isomers, due to the following factors:
the presence of asymmetrical carbon atoms,
the relative spatial arrangement of the groups in position 1 and 3 of the cyclopropane ring (cis or trans),
the isomery E or Z when there is a double bond in the substituent in position 3 (Y'=

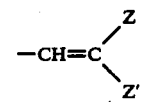

and Z is different from Z').

Within the scope of this invention there fall both the isomeric mixtures of the compounds of formula I as well as the single isomers.

As previously indicated, the compounds of formula I, wherein $R=OR^2$ are pyrethroids endowed with a high insecticide and acaricide activity besides having a good persistence.

Thus, they are useful for fighting infestations of noxious insects both in agricultural as well as in the domestic field, such as: hemiptera, lepidoptera, coleoptera, diptera and blattoidea, besides being well suited for fighting acari infestations.

For practical uses the pyrethroids of formula I may be employed either as such or in the form of suitable compositions.

Said compositions, besides the active principle, represented by one or more of the pyrethroids of formula I, also comprise a solid or liquid vehicle and, optionally, surfactants and other additives.

If desired, it is possible to add to the composition other active substances such as for instance other insecticides, acaricides or fungicides.

The pyrethroids prepared according to this invention may be formulated, according to known techniques, as dry or wettable powders, as granulates, emulsifyable concentrates, as sprays, etc.

The quantity of pyrethroids of formula I that would be useful for fighting insect or acari infestations, depends on various different factors such as the relative efficacy of the single compound used, the type of composition or formulation, the type of insect or acari to be fought, the place of the infestation, climatic and environmental conditions, the frequency of the treatments. In general, the doses to be applied may be comprised between 1 and 500 g/ha.

In order to still better illustrate the inventive idea of this invention, there will now be given a set of examples.

EXAMPLE 1

Preparation of α-cyano-3-phenoxy-benzyl ester of (±) cis, trans-2,2-dimethyl-3-(1,2-dibromo-4,4-dichloro-3-butenyl)-cyclopropanecarboxylic acid (compound n. 1):

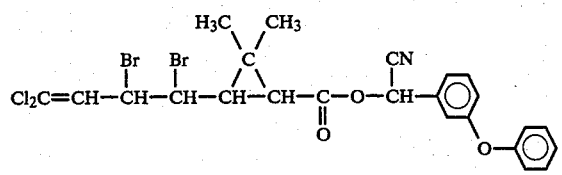

Into a flask of 100 ml holding capacity, provided with a magnetical stirrer and a dripping funnel, there were introduced, under a nitrogen atmosphere, 2.2 g of alpha-cyano-3-phenoxybenzyl ester of (±) cis, trans-2,2-dimethyl-3-(E,Z-4,4-dichlorobutadienyl)-cyclopropanecarboxylic acid (described in Italian patent application No. 27542 A/79) dissolved in 15 ml of carbon tetrachloride ($CCl_4$).

The resulting solution was thereupon cooled down to between 0°–1° C. by means of an external bath of water and ice, and at this temperature there was then slowly added in 50 minutes a solution of 0.8 g of bromine ($Br_2$) dissolved in 5 ml of $CCl_4$.

Once the addition had been completed, the solution was maintained under stirring for a further 45 minutes, allowing the temperature to rise to about 20° C.

The solvent was thereupon evaporated under reduced pressure, thereby obtaining 3 grams of the desired product. The elementary analysis proved to be consistent with the assigned structure.

$^1$H NMR ($CDCl_3$, TMS)

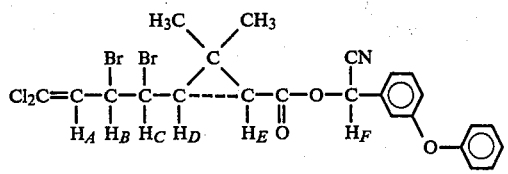

δ, ppm:
1.05–1.45 (m, 6H, geminal methyls)
1.5–2.1 (m, 2H, $H_D+H_E$)
3.6–4.05 (m, 1H, $H_C$)
4.2–5.3 (m, 1H, $H_B$)
6.0–6.3 (m, 1H, $H_A$)
6.4 (s, 1H, $H_F$)
6.9–7.6 (m, 9H, aromatic protons)
(s=singlet, m=multiplet).

EXAMPLE 2

Preparation of α-cyano-3-phenoxy-benzyl ester of (±) cis, trans-2,2-dimethyl-3-(E,Z-1,2-dibromo-4-fluoro-4-trifluoromethyl-3-butenyl)-cyclopropanecarboxylic acid (compound n. 2).

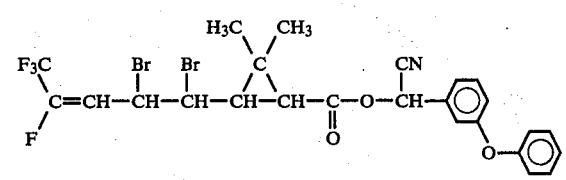

The compound was prepared by addition of bromine to the compound α-cyano-3-phenoxy-benzyl ester of (±) cis, trans-2,2-dimethyl-3-(E,Z-4-fluoro-4-trifluoromethyl-1,3-butadienyl)cyclopropanecarboxylic acid (described in Italian patent application No. 27542 A/79).

The experimental procedure was analogous to the one described in Example 1.

Elemental analysis consistent with the assigned structure.

IR strong bands at 1735, 1585, 1485, 1250, 1205, 1160, 1070, 780, 760 and 690 ($cm^{-1}$)

EXAMPLE 3

Determination of the biological activity.

The compounds of this invention were tried out on larvae or adults of the following species of insects, following the methodologies described hereunder.

For exemplyfying purposes, the data of compounds 1 and 2 have been reported on the following Table 1, and have been expressed as mortality percentages of the insects at the indicated doses.

(A) Biological activity on *Macrosiphum euphorbiae* (aphides).

Potato plants, grown in pots, were infested with adult female aphides.

The infested plants were subdivided into two groups of which one was treated, after a few hours after infestation, by besprinkling with a hydroacetonic solution (20% of acetone by volume) of the product under examination.

The percentage of the mortality of the aphides was evaluated in comparison with that of the aphides on untreated plants, after 24 hours from the moment of treatment.

(B) Biological activity on *Leptinotarsa decemlineata* (lepidoptera).

Small potato plants, grown in pots, were infested with larvae of 4 days old lepidoptera. The infested plants were subdivided into two groups one of which was treated by besprinkling with a hydroacetonic solution of the product under examination.

The percentage of mortality of the larvae was evaluated in comparison with the mortality percentage of the larvae on untreated plants, 48 hours after treatment.

(C) Biological activity on *Culex pipiens* larvae (diptera).

Into glass containers filled with pure water and into other similar vessels containing an aqueous dispersion of the product under examination, there were introduced larvae of the third and fourth age.

The percentage of mortality of the larvae was assessed 24 hours after treatment, in comparison with the mortality percentage of the larvae in the containers filled with pure water.

(D) Biological activity on *Spodoptera littoralis* (Lepidoptera)

Cut off tobacco leaves were subdivided into two groups one of which was besprinkled with a hydroacetonic dispersion of the product under examination.

After drying, all the leaves were infested with 5 days old lepidoptera larvae.

The percentage of mortality of the larvae was evaluated after 48 hours, in comparison with the mortality percentages of the larvae on the untreated leaves.

(E) Biological activity on *Musca domestica* (Diptera)

4 days old adult insects were subdivided into two groups. One of the groups was treated, by topical application with a microsyringe, with an acetonic solution of the product under examination.

The other group of insects was treated with acetone only. The mortality percentage of the insects treated was determined 24 hours after treatment by comparison with that of the insects treated only with acetone.

TABLE 1

Mortality percentage of insects treated with compound 1 and 2, at the indicated doses.

| Insect | Dose | Mortality % Compound 1 | Compound 2 |
|---|---|---|---|
| *Macrosiphum euphorbiae* | 0.1°/$_{oo}$ | 100 | 100 |
| *Leptinotarsa decemlineata* | 0.1°/$_{oo}$ | 100 | 100 |
| *Culex pipiens* larvae | 0.2 ppm | 100 | 100 |
| *Spodoptera littoralis* | 0.1°/$_{oo}$ | 100 | 100 |
| *Musca domestica* | 0.1 γ/ins | 100 | 85 |

What we claim is:
1. A compound of the general formula

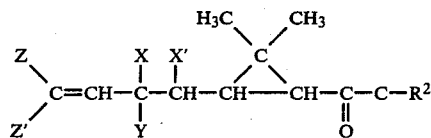

wherein:
X and X' (equal to or different from each other) are: Cl or Br;
Y is: H, F, Cl, or Br;
Z is: F, Cl, Br, CH$_3$ or CF$_3$
Z' is: F, Cl, Br or CF$_3$
R$^2$ is:

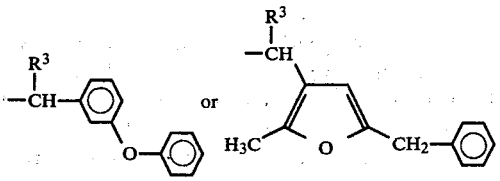

and
R$^3$ is: H, CN, or —C≡CH.

2. A compound according to claim 1 in which R$^2$ is

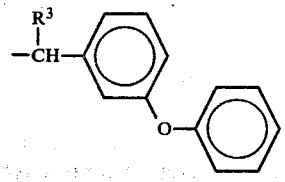

and R$^3$ is H or CN.

3. The compound α-cyano-3-phenoxy-benzyl ester of (±) cis, trans-2,2-dimethyl-3-(E,Z-1,2-dibromo-4-fluoro-4-trifluoromethyl-3-butenyl)-cyclopropanecarboxylic acid.

4. The compound α-cyano-3-phenoxy-benzyl ester of (±) cis, trans-2,2-dimethyl-3-(1,2-dibromo-4,4-dichloro-3-butenyl)-cyclopropanecarboxylic acid.

5. A method for fighting infestations by insects and acari, consisting in spreading over the zone or on the cultivation to be protected, one or more of the compounds of claim 1, either as such or in the form of suitable compositions or formulations, in an effective amount.

6. An insecticide and acaricide composition comprising an effective amount of one or more compounds of claim 1 as an active ingredient, and a vehicle.

* * * * *